(12) United States Patent
Wallis et al.

(10) Patent No.: US 8,667,855 B2
(45) Date of Patent: Mar. 11, 2014

(54) INLET SAMPLING METHOD AND DEVICE

(75) Inventors: Eric Charles Wallis, Rock Hill, SC (US); Paul J. Rauch, Charlotte, NC (US); Matthew Todd Griffin, Indian Land, SC (US); John Michael Alfred Petinarides, Waxhaw, NC (US)

(73) Assignee: Chemring Detection Systems, Inc., Charlotte, NC (US)

( * ) Notice: Subject to any disclaimer, the term of this patent is extended or adjusted under 35 U.S.C. 154(b) by 785 days.

(21) Appl. No.: 12/813,161

(22) Filed: Jun. 10, 2010

(65) Prior Publication Data

US 2011/0303024 A1    Dec. 15, 2011

(51) Int. Cl.
*G01N 1/22* (2006.01)
(52) U.S. Cl.
USPC ...................................................... 73/863.21
(58) Field of Classification Search
USPC ...................................................... 73/864.73
See application file for complete search history.

(56) References Cited

U.S. PATENT DOCUMENTS

| | | |
|---|---|---|
| 3,020,975 A | 2/1962 | Lupfer |
| 3,084,120 A | 4/1963 | Cecil et al. |
| 3,592,562 A * | 7/1971 | Spliethoff .................. 73/863.12 |
| 4,336,722 A * | 6/1982 | Schweitzer ................ 73/863.12 |
| 4,970,905 A * | 11/1990 | McClennen et al. ....... 73/864.34 |
| 5,824,919 A * | 10/1998 | Hansen ...................... 73/863.23 |
| 5,952,652 A | 9/1999 | Taylor et al. |
| 6,483,108 B1 | 11/2002 | Sakairi |

OTHER PUBLICATIONS

International Search Report for International Application No. PCT/US2011/39798, mailed Nov. 2, 2011.
Written Opinion for International Application No. PCT/US2011/39798, mailed Nov. 2, 2011.

* cited by examiner

*Primary Examiner* — Hezron E Williams
*Assistant Examiner* — Mark A Shabman
(74) *Attorney, Agent, or Firm* — Hunton & Williams LLP

(57) ABSTRACT

An inlet apparatus is disclosed. The apparatus may include a first conduit for sampling, and a second and third conduit for directing flow throughout the inlet apparatus. Flow may be induced in two opposite directions through the second conduit, which affect the flow of gas through the first conduit for sampling. The various conduits of the apparatus may be connected to a device for inducing flow in different directions. The duration of the flow in a particular direction affects the amount of sample gas that enters a detection device.

10 Claims, 7 Drawing Sheets

INLET SAMPLING METHOD AND DEVICE

FIELD OF THE EMBODIMENTS

The exemplary embodiments relate generally to a method and device for sampling ambient air. More particularly, the present embodiments relate to adjusting the dynamic range of a sampling inlet.

BACKGROUND OF THE EMBODIMENTS

Current events underscore the need for an improved and inexpensive analytical device capable of rapidly, reliably, and accurately detecting explosives, toxic chemicals, biological agents, chemical warfare agents, and other harmful materials. Spectrometers based on ion mobility have been previously developed to serve this purpose, but technological improvements are still needed to reduce detection time, increase sensitivity, enable environment adaptability, reduce noise interference, improve prediction accuracy, and reduce power consumption.

Conventional spectrometers typically employ either ion-mobility spectrometry (IMS) or differential ion mobility spectrometry (DMS) as the broad method by which they identify compounds in a sample gas taken from an ambient environment. Conventional IMS devices, which are well known in the art, are based on time-of-flight (TOF-IMS) analysis. TOF-IMS identifies compounds by measuring the time it takes ions to travel through a drift tube, usually on the order of milliseconds, from a shutter-gate to a detector electrode. The drift time is dependent on the mobility of the ions in a linear, low electric field, which accelerates the ions in the drift tube. The measured drift time is characteristic of the ion species present in the sample. In IMS systems, an ion's mobility coefficient is independent of the electric field strength but its velocity is proportional to the electric field strength.

DMS devices operate by characterizing chemical substances using differences in the gas phase mobilities of ions in alternating, high-frequency, asymmetric electric fields. Ions are separated as they are carried by drift gas between two-parallel plates or filter electrodes. At higher electric field strengths there is a nonlinear dependence on ion mobility. A high-frequency asymmetric electric field is produced by applying a high-frequency asymmetric differential potential between the plates. An equivalent field could be produced by applying a differential potential to both plates relative to ground, or to one of the plates with the other grounded. This applied field, referred to as the separation or dispersion voltage, causes ions to oscillate perpendicular to the gas flow. Some ions traverse the filter electrodes, while others gradually move towards one of the electrodes and eventually collide with an electrode, which neutralize the electric charge in such ions. Only ions with a net velocity or differential mobility of zero transverse to the applied electric field will pass through the electrodes.

Despite the differences between various IMS and DMS systems, each system may share some of the same components. Both IMS and DMS based devices may use similar inlet systems to control the flow of chemical vapor into the system and to filter water vapor and other molecules that inhibit the ability of systems to effectively detect certain chemical vapors in a gas.

These inlet systems frequently employ gas-permeable membranes to selectively block certain molecules from passing into the IMS or DMS systems. But these inlet systems have disadvantages—a set dynamic range, restrictive flow, chemical-specific limitations.

SUMMARY OF THE EMBODIMENTS

The present disclosure provides a number of exemplary embodiments that may be used collectively, in various combinations, or alone. The following summary provides examples of such inventions, and does not limit the invention as claimed in any way.

In one exemplary embodiment an inlet assembly is provided. The inlet assembly comprises a first pathway partially defined by a first conduit, a second pathway partially defined by one or more directional flow conduits that are coupled to a second and third conduit, wherein the one or more directional flow conduits comprise one or more flow regulators, the flow regulators are capable of operating in a first position in which fluid circulates from the third conduit through the second pathway to the second conduit.

In another exemplary embodiment a method of sampling is disclosed. The method comprising introducing fluid from an ambient environment into an inlet assembly, transitioning between a first step and a second step, wherein the first step comprises directing the fluid through a plurality of conduits in the inlet assembly in which the fluid flows concurrently along a flow path defined by the plurality of conduits; and the second step comprises directing fluid through the plurality of conduits in the inlet assembly in which the fluid flows countercurrently along a portion of a flow path defined by the plurality of conduits.

Other uses and variations of the foregoing will be apparent to one of ordinary skill in the art.

BRIEF DESCRIPTION OF THE DRAWINGS

Advantages of the exemplary embodiments will be apparent to those of ordinary skill in the art from the following detailed description together with the appended drawings, in which like reference numerals are used to indicate like elements.

DESCRIPTION OF THE EMBODIMENTS

Figure 1:
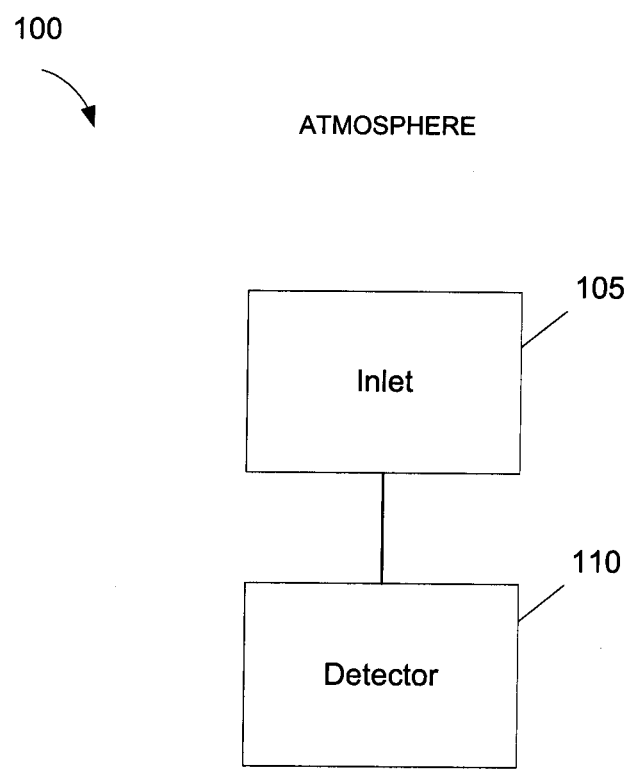
FIG. 1 illustrates a block diagram of an exemplary device for receiving gas from an ambient environment through an inlet.

The following description provides an understanding of embodiments that relate to a method and device for inlet sampling. More particularly, the embodiments relate to a variable gain sampling system, method, and device. The method and device are not limited to these exemplary embodiments, however. One of ordinary skill in the art, after reading the following description, will appreciate the exemplary embodiments for their intended purposes and their beneficial use in a number of alternative embodiments.

Terminology used for describing particular embodiments is not intended to limit the scope of an exemplary embodiment. As used throughout this disclosure, the singular forms "a," "an," and "the" include the plural, unless the context clearly dictates otherwise. Thus, for example, a reference to "a conduit" includes a plurality of conduits, or other equivalents or variations known to those skilled in the art. Furthermore, if in describing some embodiments or features permissive language (e.g., "may") is used, that does not suggest that embodiments or features described using other language (e.g., "is," "are") are required. Unless defined otherwise, all terms have the same commonly understood meaning that one of ordinary skill in the art to which this invention belongs would expect them to have.

The accompanying figures and following description depict and describe exemplary embodiments of an inlet sampling device with features that may provide for dynamic sampling. As used throughout this description, the term "sampling device" or other like terms is meant to encompass any inlet for any device having the features described herein.

With regard to the exemplary embodiments of the inlet device described below, any part that fastens, inserts, attaches, or connects any component to or from the device (or another device) is not limited to any particular type and is instead intended to encompass all known and conventional fasteners, like screws, nut and bolt connectors, threaded connectors, snap rings, detent arrangements, clamps, rivets, toggles, and so on. Fastening may also be accomplished by other known fitments, like leak-tight seals or sealing devices. Components may also be connected by adhesives, polymers, copolymers, glues, welding, ultrasonic welding, and friction fitting or deformation. This is not an exhaustive list and any combination of these fitment systems can be used.

Unless otherwise specifically disclosed, materials for making components of the present invention may be selected from appropriate materials, such as metal, metal alloys, natural or manmade fibers, composites, vinyl, plastics, silicone, rubber, and so on. Any and all appropriate manufacturing or production methods, such as casting, pressing, extruding, molding, machining, may be used to construct the exemplary embodiments or their components.

When describing exemplary embodiments, any reference to relative position (front and back or rear, top and bottom, right and left, upper and lower, and so on) is intended to conveniently describe those embodiments only. Positional and spacial references do not limit the exemplary embodiments or its components to any specific position or orientation.

The exemplary embodiments described herein may have particular application to an apparatus for dynamic sampling. Generally, the exemplary embodiments provide for apparatus and method to adjust for the amount and type of sample gas that is passed to the spectrometer. The exemplary embodiments may alternate between one or more modes (e.g., a first and second mode). In an exemplary embodiment, one mode may be considered a re-circulating mode, whereas the other mode may be considered a sampling mode. The re-circulating mode may control the flow of air through one or more conduits of the device in a way that increases the possibility that clean, filtered gas enters a detection device. The sampling mode may affect the flow of air through one or more conduits of the device to allow gas to flow directly from the atmosphere to a detection device.

FIG. 1 illustrates a block diagram that shows an exemplary embodiment of a device 100 that may be used to detect certain components present in the surrounding ambient air by analyzing a sample taken from the ambient environment. This sample may be referred to as "sample gas" may be introduced into the device 100 from the atmosphere. In an exemplary embodiment, the device 100 may comprise an inlet region 105 and a detection region 110.

In operation, sample gas may be introduced to an inlet region 105 of the device 100 from an ambient air environment. The inlet region 105 may be responsible for allowing sample gas from the environment to pass into the detector region 110. In an exemplary embodiment, the inlet region 105 may serve one or more functions. In an exemplary embodiment, it may serve two functions: sample collection and introduction. The inlet region 105 may also concentrate the sample, filter the sample, or provide a selective barrier between the detector region 110 and the environment.

The inlet region 105 may operate in a number of states. In an exemplary embodiment, various operational states of inlet region 105 may allow either a maximum or a minimum amount of sample gas to pass through to the detector region 110. Inlet region 105 may also operate to prevent any gas from the atmosphere from entering the device 100. In additional exemplary embodiments, inlet region 105 may operate in a sampling mode, a re-circulating mode, or it may alternate between a sampling mode and a re-circulating mode.

Detector region 110 may detect one or more components within gas sampled from an ambient air environment. The ambient air environment may be air inside or outside of a building, for example. The components that may be detected include, but are not limited to, chemical warfare agents, nerve agents, blister agents, choking agents, toxic industrial chemicals (TICs), toxic industrial materials (TIMs), low vapor pressure compounds, explosives, narcotics, and/or combinations thereof. Detector region 110 may also detect organic chemicals, hydrocarbons, and/or combinations thereof. The detector region 110 may be used in various applications and may be designed to meet the detector requirements of various jurisdictions, such as the requirements of the United States government and the Canadian Government, for example. The detector region according to the present embodiments is not required to meet these requirements, however.

Detector region 110 may be configured to analyze a sample gas to detect vapors in any number of ways. In an exemplary embodiment, the detector 110 may be a differential mobility spectrometer (DMS) detector, a field asymmetric ion mobility spectrometry (FAIMS) detector, a field ion spectrometry (FIS) detector, a radio frequency ion mobility spectrometry (RFIMS), or any other type of detector capable of analyzing a gas. Exemplary embodiments include ionization of the sample gas to generate ions or analytes of chemical species present in the sample gas. In this embodiment, the ions may pass through a pair of oppositely charged collector electrodes, one positive and one negative.

Inlet region 105 and detector region 110 may be connected to one another in any number of ways. In one exemplary embodiment, a conduit may connect inlet region 105 to detector region 110 via an adaptor. In another exemplary embodiment, inlet region 105 may be sealed within a housing for detector region 110. In an additional exemplary embodiment, detector region 110 may be coupled to inlet region 105 by any type of conduit or air-flow system. In yet another exemplary embodiment, inlet region 105 and detector region 110 may be coupled together by an air pressure system capable of inducing pressure differentials within device 100.

Figure 2A:
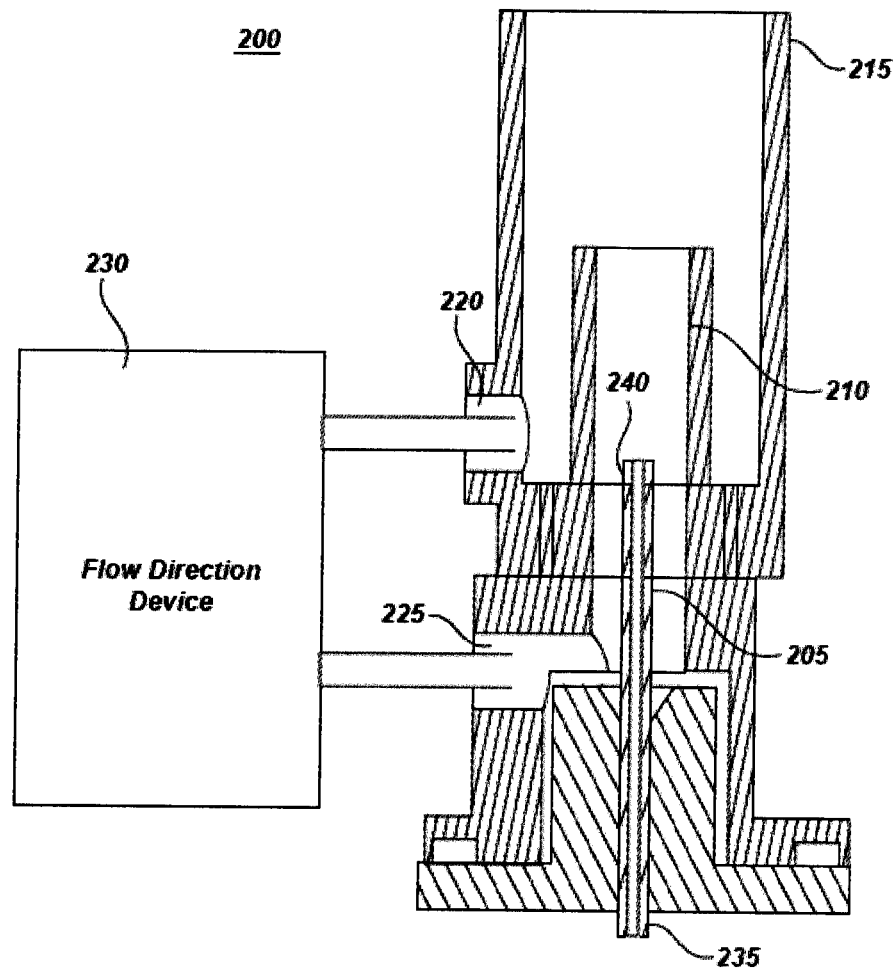
FIG. 2(a) is a cross-sectional view of a variable gain sampling inlet apparatus, according to exemplary embodiment of the present disclosure.

Referring to FIG. 2, an exemplary embodiment of an inlet device 200 is depicted. This device 200 may be variable gain sampling device and may be similar to the inlet device 105, as discussed above with reference to FIG. 1. Components of the variable gain sampling inlet device 200 may include: a first conduit 205, a second conduit 210, and a third conduit 215. The variable gain inlet device 200 may also include directional flow conduits 220 and 225. Furthermore, variable gain inlet device 200 may include a flow direction device 230, also known or referred to as a flow regulator.

First conduit 205 may have an open orifice end 240 and a connection end 235. Connection end 235 may be connected to any type of detecting device. The open orifice 240 of first conduit 205 may be located entirely within second conduit 210. In another exemplary embodiment, the orifice 240 of first conduit 205 may extend beyond the orifice of second conduit 210. In yet another embodiment, the orifice 240 of first conduit 205 may extend beyond the open orifices of both second conduit 210 and third conduit 215. In other exemplary embodiments, the orifices of first conduit 205, second conduit 210 and third-conduit 215 may be coplanar.

Those skilled in the art will understand that the width of first conduit 205 may vary to support any number of applications. In an exemplary embodiment, the width of first conduit 205 may be dynamically controlled by any number of width control devices, such as valves or diaphragms (not shown). The width control devices may be capable of expanding or contracting to adjust the flow of air through first conduit 205. The width control devices may be automatically or manually adjusted, according to changes in pressure, temperature, saturation, or desired flow. Furthermore, the width control devices may control direction through the device by restricting or permitting flow.

The open orifice end 240 of first conduit 205 may protrude into second conduit 210. First conduit 205 may be connected or sealed to second conduit 210 in any number of ways. For example, first conduit 205 may be hermetically sealed to second conduit 210. In another exemplary embodiment, first conduit 205 may be vacuum sealed to second conduit 210. In another exemplary embodiment, first conduit 205 may be sealed to second conduit 210 by rubber or elastomeric seals. The various exemplary sealing techniques may operate to restrict air-flow through first conduit 205, to prevent gas leakage, or to allow a certain amount of acceptable or desired gas leakage.

First conduit 205 may be connected to either second conduit 210 or third conduit 215. First conduit 205 may be connected to second conduit 210 and/or third conduit 215 in any number of ways. By way of a non-limiting example, first conduit 205 may be connected to a housing, which also connects to second conduit 210 and/or third conduit 215. Further, first conduit 205 may also connected to second conduit 210, third conduit 215, and/or any number of receiving devices (such as detector 110, as shown in FIG. 1) by any number of valve or seals (not shown). The valves or seals may be of any material, including rubber or elastomer. The valves or seals may operate to restrict air-flow through first conduit 205, to prevent leakage, or to allow a certain amount of acceptable or desired leakage.

First conduit 205 may be made of any number of materials, or any combination of materials, including, for example, polypropylene, polyetheretherketone, fused silica, fluorinated ethylene propylene, or stainless steel and other metals. Those skilled in the art will understand that first conduit 205 may be made of any number of materials, or any combination of materials, to support any number of a variety of applications.

Second conduit 210 may be located inside of third conduit 215. Second conduit 210 may be connected to first conduit 205, third conduit 215, and directional flow conduits 220 and 225. Furthermore, second conduit 210 may be connected to flow direction device 230 through third conduit 215, directional flow conduits 220 and 225 or it may connect directly to flow direction device 230. In an exemplary embodiment, second conduit 210 may be wider than first conduit 205, so that first conduit 205 may be located within second conduit 210. In another exemplary embodiment, second conduit 210 may be narrower than third conduit 215, so that second conduit 210 may be located within third conduit 215.

Second conduit 210 may be made of any number of materials, or any combination of materials, including, for example, polypropylene, polyetheretherketone, fused silica, flourinated ethylene propylene, and stainless steel or other metals. Those skilled in the art will understand that second conduit 210 may be made of any number of materials, or any combination of materials, to support any number of a variety of applications. Second conduit 210 may be made out of the same material as first conduit 205, or it may be made out of a different material.

Second conduit 210 may be connected to first conduit 205, third conduit 215, directional flow conduits 220 and 225, and/or flow direction device 230. In an exemplary embodiment, second conduit 210 may be connected to the same housing as first conduit 205 and/or third conduit 215. In another exemplary embodiment, the second conduit 210 may be connected to the other conduits and devices through seals, valves, or other connecting means. The valves, seals, or other connecting means may be made of any material, including rubber or elastomer. The valves, seals, or other connecting means may operate to restrict air-flow through second conduit 210, to prevent leakage, or to allow a certain amount of acceptable or desired leakage.

The width and length of second conduit 210 may be adjusted for any number of reasons. In one embodiment, the width of second conduit 210 may be twice as large as the width of first conduit 205. In another exemplary embodiment, the width of second conduit 210 may be only slightly larger than the width of first conduit 205. In another exemplary embodiment, the width of second conduit 210 may be much larger than first conduit 210. It will be apparent to those skilled in the art that the width of second conduit 210 may be adjusted in reference to first conduit 205, third conduit 215, and directional flow conduits 220 and 225 to adjust the flow of air through variable gain sampling inlet device 200. Further, diaphragms and valves (not shown) may be located within second conduit 210 to adjust air flow quantity and direction through device 200. The diaphragms and valves (not shown) may be automatically or manually adjusted, according to changes in pressure, temperature, saturation, or desired flow. Furthermore, the valves or diaphragms (not shown) may control direction through the system by restricting or permitting flow.

Third conduit 215 may be located outside of second conduit 210 and first conduit 205. Third conduit 215 may be connected to first conduit 205, second conduit 210, and/or directional flow conduits 220 and 225. Furthermore, third conduit 215 may be connected to flow direction device 230 through directional flow conduit 220. In an exemplary embodiment, third conduit 215 may be wider than first conduit 205 and second conduit 210, so that both first conduit 205 and second conduit 210 may be located within third conduit 215.

In an exemplary embodiment, directional flow conduits 220 and 225 connect second conduit 210 and third conduit 215 to flow direction device 230. In an additional exemplary embodiment, directional flow conduits 220 and 225 may be connected to the same housing as first conduit 205, second conduit 210, and/or third conduit 215. In another exemplary embodiment, directional flow conduits 220 and 225 may be connected to flow direction device 230. This connection may be formed in any number of ways. For example, directional flow conduits 220 and 225 may be directly connected to flow direction device 230. In another exemplary embodiment, flow conduits 220 and 225 may be connected to flow direction device 230 through an air distribution system (not shown). The connection between flow conduits 220 and 225 and flow direction 230 may be sealed in any number of ways. In an exemplary embodiment, flow direction device 230 may be hermetically sealed to flow conduits 220 and 225. In another exemplary embodiment, flow conduits 220 and 225 may be sealed to flow direction device 230, second conduit 210 and third conduit 215 by any number of valves, seals or any other connecting means.

The width and length of directional flow conduit 220 and 225 may be adjusted for any number of reasons. In an exemplary embodiment, the width of flow conduit 220 and flow conduit 225 may differ. In another exemplary embodiment, the width of flow conduit 220 and flow conduit 225 may be the same. It will be apparent to those skilled in the art that the width of directional flow conduits 220 and 225 may be adjusted to affect the flow of air through variable gain sampling device 200. Further, in an exemplary embodiment, diaphragms and valves (not shown) may be located within directional flow conduit 220 and 225 to adjust air flow quantity and direction through device 200. The diaphragms and valves (not shown) may be automatically or manually adjusted, according to changes in pressure, temperature, saturation, or desired flow. Furthermore, the valves or diaphragms (not shown) may control direction through the system by restricting or permitting flow.

Flow direction device 230 may direct flow in any number of ways. By way of a non-limiting example, flow direction device 230 may direct flow using one or more air-pumps. In another exemplary embodiment, flow direction device 230 may direct flow through a series of valves, which adjust pressure differentials throughout the system. Flow direction device 230 may contain various sub-components for controlling the flow of gas throughout the various conduits of device 200. Flow direction device 230 may also contain a number of additional sub-components, which may control the level of moisture and contaminates throughout the airflow within the system. Those skilled in the art will understand that flow direction device 230 may be configured in any number of ways to direct the flow of gas through the device 200. Other exemplary embodiments of flow direction device 230 are discussed in more detail below, with regard to FIG. 3.

Figure 2B:
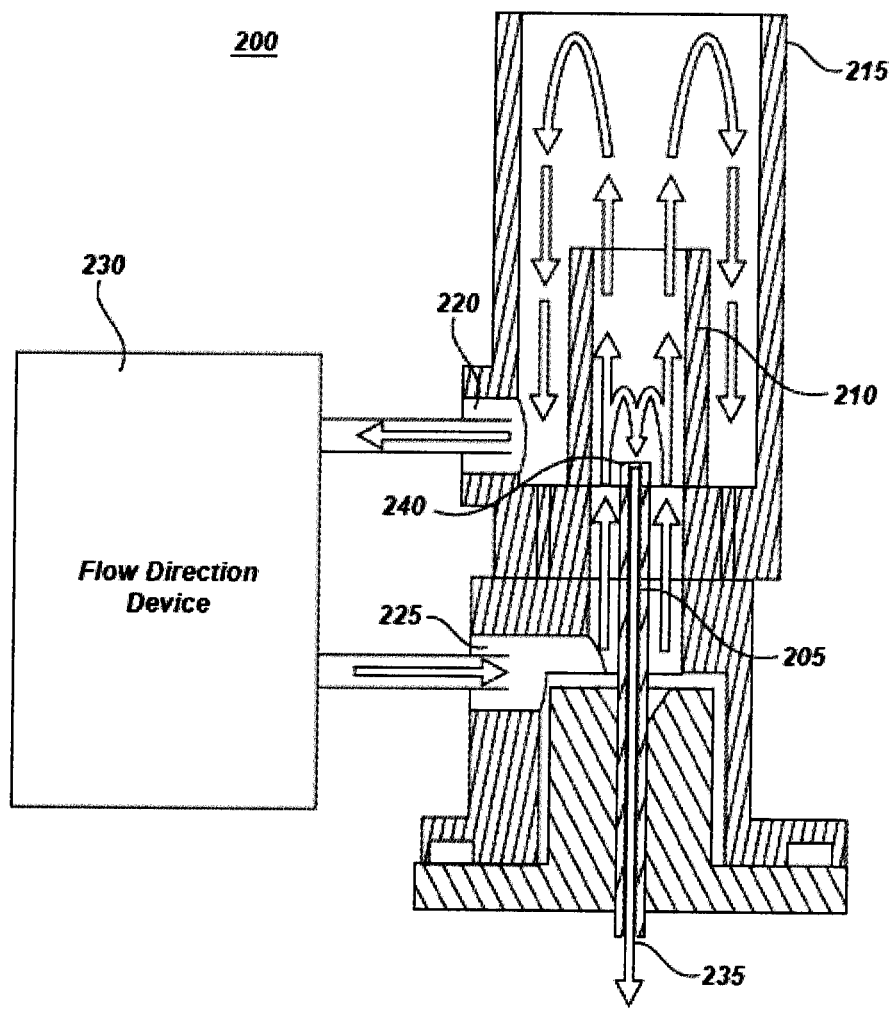
FIG. 2(b) illustrates an exemplary variable gain sampling inlet apparatus operating in a first mode.

FIG. 2(b) illustrates an exemplary embodiment of a variable gain sampling inlet device 200 operating in a first mode, which may be referred to as a re-circulating mode. While in the re-circulating mode, flow direction device 230 may affect flow throughout inlet device 200 according to a re-circulating mode flow pattern. In one embodiment, during re-circulating mode, gas from the outside environment (atmosphere) will not enter into inlet device 200. In this embodiment, air from the outside atmosphere may not pass by or through first conduit 205. Therefore, during re-circulating mode, an attached detector device, such as detector 110 depicted in FIG. 1, may not intake sample gas from the ambient atmosphere.

While operating in re-circulating mode, flow direction device 230 may direct flow to directional flow conduit 225 and may receive flow from directional flow conduit 220. In an exemplary embodiment, gas may flow from directional flow conduit 225 to second conduit 210. Further, gas may pass by the orifice 240 of first conduit 205, with a portion of the gas flow entering into first conduit 205 and the remaining gas continuing through the second conduit 210. The remaining gas may then flow into third conduit 215, where it may pass into directional flow conduit 220. Gas passing through directional flow conduit 220 may pass into the flow direction device 230, where it may later re-enter the second conduit through directional flow conduit 225. Continuing this exemplary flow pattern, gas passing through first conduit 205 may also pass through flow direction device 230, where it may then re-enter the system by passing through directional flow conduit 225.

During re-circulating mode, the flow through second conduit 210 may be in the opposite direction of the flow through first conduit 205. This flow may be countercurrent along a portion of the flow path. This flow pattern may create a sheath gas near the opening of first conduit 205. In this embodiment, the sheath gas may be substantially clean of contaminants and dry. This gas may flow through the first conduit 205 and pass through first conduit connecting end 235 to a detector, such as detector 110 depicted in FIG. 1. This detector may continuously sample this clean, dry sheath gas. In doing so, the detector system may remain clean and ready for detection of chemical vapors once the flow of air through first conduit 205 is altered to introduce unfiltered gas from the atmosphere into the system.

In a exemplary embodiment, flow direction device 230 may contain a scrubbing device and/or a drying device (shown in more detail in FIG. 3), which may scrub and remove moisture from the air during re-circulation mode to allow substantially clean, dry air enters the detection device through first conduit 205. Also, flow direction device 230 may cause the air in third conduit 215 to flow in the same direction as the air flow in first conduit 205. That is, the flow may be concurrent. This air flow pattern may capture excess sheath gas, which may be re-circulated through flow direction device 230.

The flow of air through device 200 during re-circulating mode may be altered in a number of ways. In an exemplary embodiment, the flow pattern may be altered to create a second sheath gas outside of the opening of second conduit 210. This second sheath gas may also pass through first conduit 205. In another exemplary embodiment, the flow of air through device 200 during re-circulating mode may be altered by adjusting the widths of any of the first conduit 205, the second conduit 210, or the third conduit 215 with diaphragms (not shown). Adjusting diaphragms may increase or decrease the air flow rate through the various conduits within device 200, which may affect the amount, flow and location of sheath gas and/or the amount and flow of gas entering a detection device through first conduit 205.

Figure 2C:
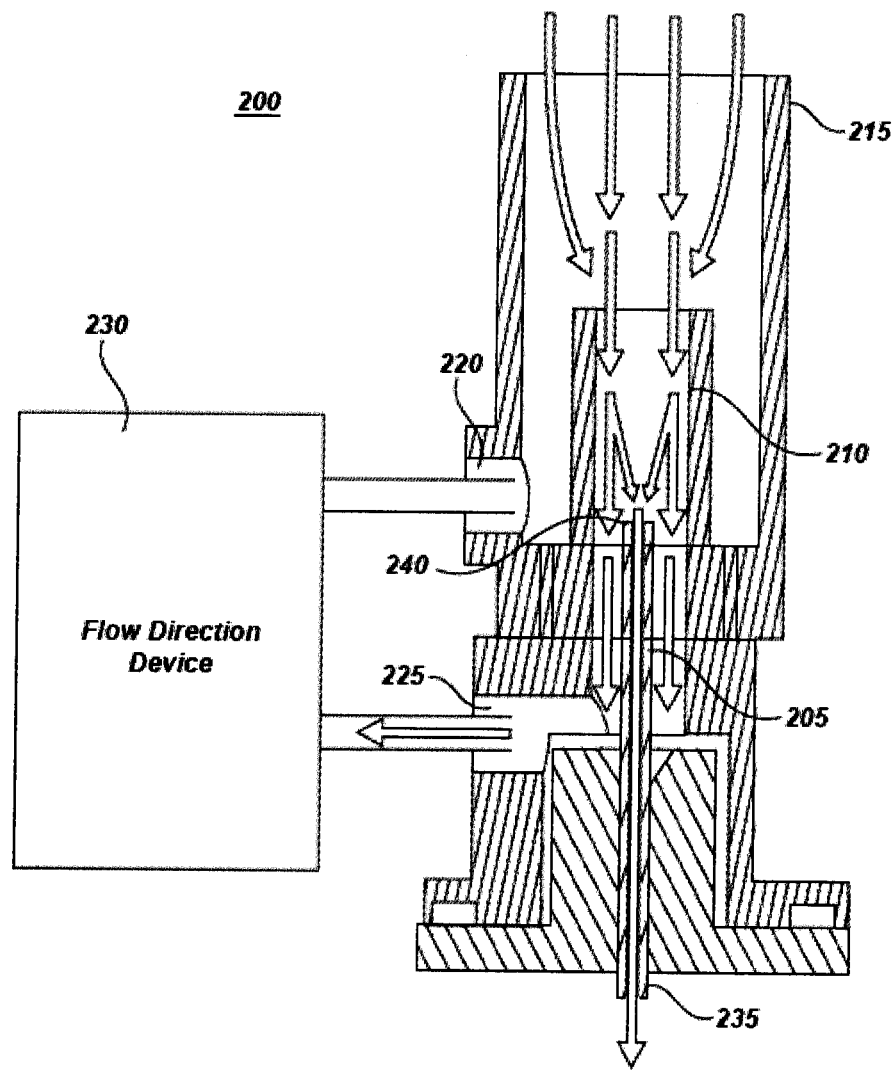
FIG. 2(c) illustrates an exemplary variable gain sampling inlet apparatus operating in a second mode.

FIG. 2(c) illustrates an exemplary embodiment of a variable gain inlet sampling device 200 operating in a second mode, which may be referred to as a sampling mode. During sampling mode, flow directional device 230 may affect the flow of air through the system so that gas is pulled from the atmosphere into device 200. In an exemplary embodiment, flow direction device 230 may pull gas directly from the atmosphere by directing flow through second conduit 210 and directional flow conduit 225.

In an exemplary embodiment, this air flow pattern may draw gas through second conduit 210. In this preferred embodiment, gas flows through second conduit 210 past the open orifice end 240 of conduit 205. A portion of this gas flow may then pass through first conduit 205, where it flows through connecting end 235 to a detecting device, such as the detector described in FIG. 1. Excess air that does not pass into first conduit 205, may continue through second conduit 210, where it may then pass through directional flow conduit 225 and onto flow direction device 230. In one exemplary embodiment, during sampling mode, excess air passing through flow direction device 230 may be discharged directly into the atmosphere to prevent the re-circulation of air through directional flow conduit 220. In another exemplary embodiment, the flow through second conduit 210 and first conduit 205 may be induced solely by a detecting device, such as detector 110 depicted in FIG. 1. In this embodiment, gas may not pass through flow direction device 230 at all.

FIG. 3(*a*) depicts a block diagram of an exemplary embodiment of a flow direction device 300 affecting re-circulating mode within the device 200. Flow direction device 300 may be similar to flow device 200, as illustrated in FIG. 2. In an exemplary embodiment, the flow direction device may include one or more scrubbers 305. Scrubber 305 may be provided to remove contaminants from the circulating gas. The scrubber 305 may be located anywhere within flow direction device 300. In another exemplary embodiment, scrubber 305 may be deployed outside of flow direction device 300. Further, in additional exemplary embodiment, scrubber 305 may be deployed within any number of conduits, such as the first, second, and third conduits described in FIG. 2(*a*).

As disclosed herein, a "scrubber" may be described as any medium or substance capable of removing contaminates from the gas. In one embodiment, the scrubber may be used to remove such contaminates and not to remove moisture from the gas. Accordingly, the scrubber 305 may comprise any medium, such as activated charcoal, capable of removing analytes and other contaminating vapors from the carrier gas in a spectrometer. It is expected that any such scrubber material will have some capacity to absorb moisture. However, according to various embodiments, it may be advantageous to use scrubbers with either low or high saturation points for moisture absorption. This characteristic may be useful to condition the scrubber 305 to a specific level of moisture, capable of maintaining the carrier gas or other gas to within a range of moisture content, required for the optimal performance of a detecting device, such as detector 110 described in FIG. 1.

Flow direction device 300 may also include a dryer 330. As disclosed herein, a "dryer" may be described as any medium or substance capable of removing moisture from the gas. The dryer 330 may be used to remove moisture, and not to remove contaminates from the gas. In another exemplary embodiment, dryer 330 may be configured to remove both moisture and contaminates from the gas flow. In an exemplary embodiment, the dryer may include a drying agent. The drying agent may be any material or desiccant capable of removing moisture from the ambient air or carrier gas used in the device 200. A molecular sieve, as is well known in the art, may be an efficient dryer and may be capable of binding water molecules to itself and not releasing it back to the carrier gas until it reaches a high saturation point. A molecular sieve may be well suited to function within flow direction device 300 to take out excess moisture from the air, and thus maintain a desired level of moisture for operating in re-circulating mode. It is recognized that a molecular sieve, or other dryer that is utilized, may also remove some contaminates.

In an exemplary embodiment, flow direction device 300 may have a pair of directional control valves 310 and 311. As depicted in FIGS. 3(*a*) and 3(*b*), directional control valves 310 and 311 may operate in several operating modes, the operating modes controlling the flow of gas through the device 200. As depicted in FIG. 3(*a*), while operating in re-circulating mode, valves 310 and 311 may be configured to receive air from an inlet, such as inlet 200 described in FIG. 2, through flow conduit 320 and to direct air back into the inlet through flow conduit 325.

As depicted in FIG. 3(*b*), the valves may be adjusted to direct the flow of gas during sampling mode. In a preferred embodiment, valve 310 may be configured to receive gas flow from flow conduit 325. This gas may then be pulled through pump 315 to a valve 311, where the gas may be discharged directly into the atmosphere. This exemplary operational mode may cause air to pass directly from the atmosphere into a detection device through a sampling inlet, such as first conduit 205 depicted in FIG. 2(*a*).

In an exemplary embodiment, the valves 310 and 311 may be controlled by a moisture sensor controller (not shown). Based on the determination of the moisture content of the gas, the moisture sensor controller may affect the valves 310 and 311 so that gas flows in either re-circulating mode or sampling mode. The moisture sensor controller may maintain the moisture level between an upper and lower threshold value as desired. Those with skill in the art will appreciate that the particular moisture range will depend on the needs of the particular conditions.

In another exemplary embodiment, the valves 310 and 311 may be controlled by a timing mechanism (not shown). The timing mechanism may be pre-programmed to adjust the position of the valves 310 and 311 according to a pre-established schedule. The timing mechanism schedule may be programmed in any number of ways, to support any number of applications. By way of a non-limiting example, the timing mechanism may be configured to operate valves 310 and 311 in re-circulating mode for a longer period of time than in sampling mode. In another embodiment, the timing mechanism may be configured to operate the valves 310 and 311 in sampling mode for a longer period than re-circulating mode. In additional embodiment, the timing mechanism may be configured to operate in re-circulating mode and sampling mode for equivalent lengths of time.

Further, in another exemplary embodiment, the valves 310 and 311 may be controlled by a contaminate-sensor controller (not shown). Based on a determination of contaminates in the gas, the contaminate-sensor controller may switch the valves 310 and 311 so that device 200 operates in either re-circulating mode or sampling mode. The contaminate sensor controller may maintain the contaminate level between an upper and lower threshold value as desired. It is appreciated that the particular moisture range will depend on the needs of the particular conditions.

Figure 3A:
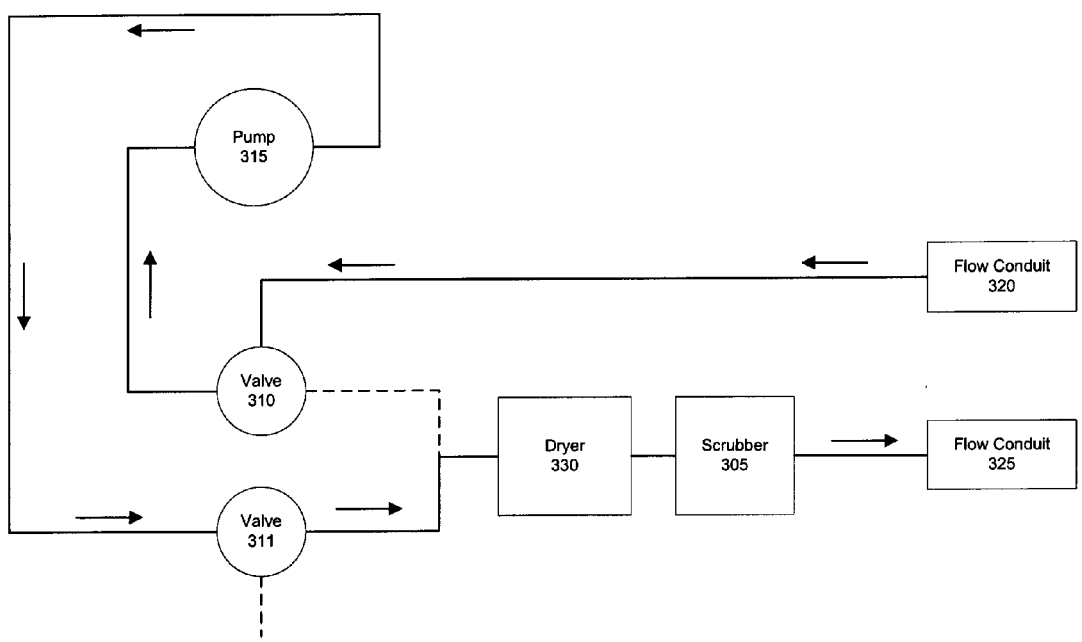
FIG. 3(a) illustrates an exemplary block diagram of a flow direction device operating in a first mode.
Figure 3B:
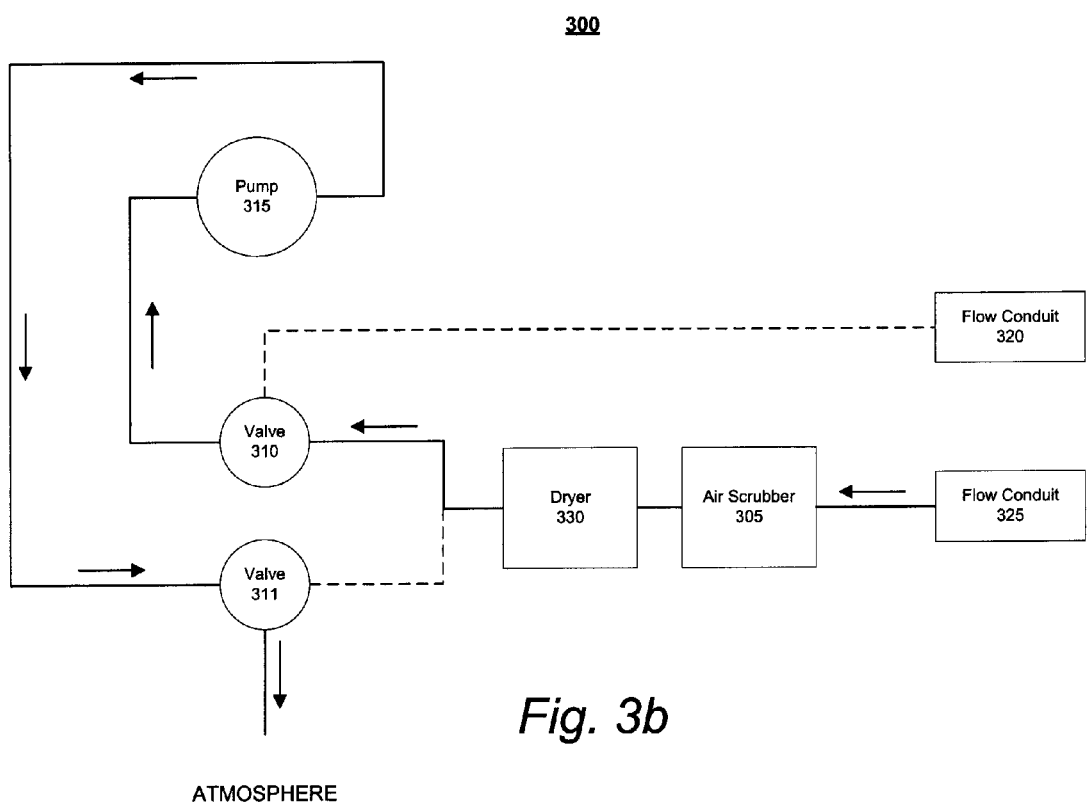
FIG. 3(b) illustrates an exemplary block diagram of a flow direction device operating in a second mode.

Still referring to FIGS. 3*a* and 3*b*, the directional flow valves 310 and 311 may be controlled by a user input actuator (not shown). In another exemplary embodiment, the valves 310 and 311 may continuously operate in a default mode, until the user input actuator receives an input. Upon receiving a user input, the actuator may switch the valves 310 and 311 to operate in a different mode. By way of a non-limiting example, the flow direction device 300 may be programmed to operate in re-circulating mode for an indefinite amount of time. Upon receiving a user input, the actuator may toggle the valves 310 and 311 to operate flow direction device 300 in sampling mode. In an exemplary embodiment, the device may then continue to operate in sampling mode until receiving a second user input, or it may operate in sampling mode for a pre-programmed period of time. Then, the actuator may affect the valves 310 and 311 to operate in re-circulating mode once again.

Figure 4:
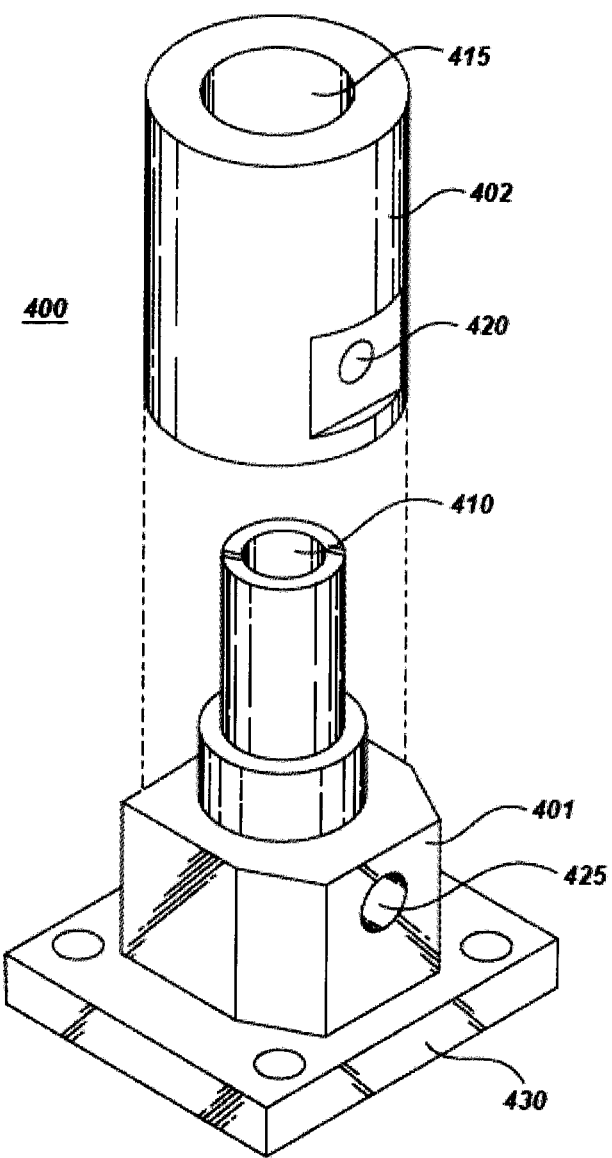
FIG. 4 illustrates an exploded view of a second and third inlet of an exemplary variable gain sampling inlet.

Referring to FIG. 4, another exemplary embodiment of an inlet 400 is shown. The inlet 400 may generally include first component 401 and second component 402. The first component 401 may comprise a base 430, a second conduit 410, and an orifice 425. In an exemplary embodiment, the orifice 425 may be coupled to a directional flow conduit or be part of a directional flow conduit (which is not shown). The first component 401 may comprises separate pieces or may be formed as an integral piece. The second component 402 may comprise a third conduit 415 and an orifice 420. In an exemplary embodiment, the orifice 420 may be coupled to a directional flow conduit or be part of a directional flow conduit (which is not shown). The first component 401 and the second component 402 may be coupled together to form the variable gain inlet 400.

In an exemplary embodiment, second component 402 may be removably connected to first component 401. In another exemplary embodiment, second component 402 and first component 401 may be integrally connected to form a single structure. Variable gain inlet 400 may be similar to variable gain inlet 200 depicted in FIG. 2a. In an exemplary embodiment, second component 402 may mate with first component 401, such that third conduit 415 surrounds second conduit 410. Further, a first conduit (not shown) may be inserted within the first component 401 to form a first conduit (not shown) similar to first conduit 205 depicted in FIG. 2a. The first conduit (not shown) may extend through the base 430 of component 401. In this embodiment, the first conduit (not shown), may couple to a detector (not shown), such as detector 110 depicted in FIG. 1. Furthermore, directional flow conduits may be coupled to a flow direction device (not shown), such as flow regulator or the flow direction device 230 depicted in FIG. 2a.

It should be understood that the foregoing embodiments are exemplary only, and other embodiments will be apparent to those of ordinary skill in the art in light of the teachings provided herein. For example, while the foregoing embodiments describe methods and devices for use in gas sampling, it will be readily apparent that these may be modified for use in other processes. Other variations will be apparent to those of ordinary skill in the art in view of the present disclosure and with practice of the invention.

The invention claimed is:

1. An inlet assembly, comprising:
   a first pathway partially defined by a first conduit;
   a second pathway partially defined by one or more directional flow conduits that are coupled to a second and a third conduit;
   wherein the one or more directional flow conduits comprise a flow direction device comprising one or more flow regulators, a first directional flow conduit between the third conduit and the flow direction device, and a second directional flow conduit between the flow direction device and the second conduit, the flow regulators being capable of operating in a first position in which fluid circulates through the second pathway from the third conduit to the second conduit and back to the third conduit, and
   wherein the one or more flow regulators are configured to allow fluid communication between the first directional flow conduit and the second directional flow conduit when the one or more flow regulators are operating in the first position.

2. The inlet assembly of claim 1, wherein the one or more flow regulators comprise one or more valves.

3. The inlet assembly of claim 1, wherein the second conduit is generally concentric to the first conduit.

4. The inlet assembly of claim 1, wherein the third conduit is generally concentric to the second conduit.

5. The inlet assembly of claim 4, wherein the second pathway is further partially defined by the interspace between the second and first conduits when the one or more flow regulators are in the first position.

6. The inlet assembly of claim 5, wherein the second pathway is further partially defined by the interspace between the third and second conduits when the one or more flow regulators are in the first position.

7. The inlet assembly of claim 1, wherein the one or more flow regulators being capable of operating in a second position in which fluid flows from an ambient environment through the first pathway.

8. The inlet assembly of claim 7, wherein one or more flow regulators direct a portion of the fluid from the ambient environment through the second conduit and into a portion of the second pathway.

9. The inlet assembly of claim 8, wherein at least some of the fluid directed through a. portion of the second pathway is purged from the inlet assembly.

10. The inlet assembly of claim 7, wherein the one or more flow regulators are configured to operate between the first and second position.

* * * * *